(12) United States Patent
Clarence-Smith et al.

(10) Patent No.: US 7,488,755 B2
(45) Date of Patent: Feb. 10, 2009

(54) DERIVATIVES OF GLYCINERGIC R(+)-2-AMINO-3-HYDROXYPROPANOIC ACID

(75) Inventors: Kathleen Clarence-Smith, Washington, DC (US); Jean-Marie Georges Contreras, Fegersheim (FR); Laurence Nathalie Deyon, Illkirch (FR); Camille Georges Wermuth, Strasbourg (FR)

(73) Assignee: Prestwick Pharmaceuticals, Inc., Washington, DC (US)

( * ) Notice: Subject to any disclaimer, the term of this patent is extended or adjusted under 35 U.S.C. 154(b) by 555 days.

(21) Appl. No.: 10/524,869

(22) PCT Filed: Aug. 1, 2003

(86) PCT No.: PCT/FR03/02447

§ 371 (c)(1),
(2), (4) Date: Feb. 11, 2005

(87) PCT Pub. No.: WO2004/016580

PCT Pub. Date: Feb. 26, 2004

(65) Prior Publication Data

US 2005/0261372 A1 Nov. 24, 2005

(30) Foreign Application Priority Data

Aug. 14, 2002 (FR) .................... 02 10306

(51) Int. Cl.
*A01N 37/12* (2006.01)
*A61K 31/195* (2006.01)
*C07C 229/00* (2006.01)

(52) U.S. Cl. .................. 514/561; 514/563; 560/19; 560/155; 562/553

(58) Field of Classification Search .............. None
See application file for complete search history.

(56) References Cited

U.S. PATENT DOCUMENTS

| 5,837,730 A | 11/1998 | Javitt |
| 5,854,286 A | 12/1998 | Javitt et al. |
| 6,228,875 B1 * | 5/2001 | Tsai et al. .................. 514/380 |

FOREIGN PATENT DOCUMENTS

| EP | 0528172 | 2/1993 |
| WO | WO 96/19457 A1 | 6/1996 |
| WO | WO98/03472 | 1/1998 |
| WO | WO 9803472 A1 * | 1/1998 |
| WO | WO 2005/077946 | 8/2005 |

OTHER PUBLICATIONS

Ariyoshi et al., "The Structure-Taste Relationships of the Dipeptide Esters Composed of L-Aspartic Acid and β-Hydroxy Amino Acids," Bulletin of the Chemical Society of Japan, vol. 47(2), 1974, pp. 326-330.
Subramanian et al., "Synthesis of oxazolidinyl azacycles via ring-closing olefin metathesis: a practical entry to the synthesis of deoxyazasugars and hydroxypyrrolizidines," Tetrahedron Letters 42 (2001), pp. 4079-4082.
Terradas et al., "Marked Dependence of Enzyme Prochiral Selectivity on the Solvent," J. Am. Chem. Soc. 1993, 115, pp. 390-396.
Robert Haner et al. ; "155. Preparation and C-Alkylation of Enantiomerically Pure S-Phenyl Aziridinecarbothioates. On the Structure of Small-Ring Ester Lithium Enolates"; Helvetica Chimica Acta, vol. 70, No. 7, 1987, pp. 1676-1693.
Susan E. Gibson et al. ; "Synthesis of Conformationally constrained Phenylalanine Analogues Via 7-, 8- and 9-endo Heck Cyclisations"; Journal of the Chemical Society, Perkin Transactions 1., No. 4, 1997, pp. 447-455.
Chemical Abstracts, vol. 76, No. 7, Feb. 14, 1972 Columbus, Ohio, US ; abstract No. 34561T, A. Balog et al, ; "Peptides. XE. Use of Serine N-Protected with beta-Dicarbonyl compounds in Peptide Synthesis" p. 347; col. 1; XP002239529 abstract -& "Formulas C6H10N8-C9H13BrPb" Chemical Abstracts (9th Collective Index), vol. 76-85, 1972-1976, p. 2920F XP002239528 Columbus Ohio, US p. 2920F, col. 3, line 84-line 85.

* cited by examiner

*Primary Examiner*—Sreeni Padmanabhan
*Assistant Examiner*—Samira Jean-Louis
(74) *Attorney, Agent, or Firm*—Howrey LLP; Viola T. Kung

(57) ABSTRACT

The use of R(+)-2-amino-3-hydroxypropanoic acid derivatives, nitrogen substituted by a ($C_1$-$C_6$)alkyl, ($C_3$-$C_6$)alkenyl, 3-oxo($C_5$-$C_6$)alkyl, 3-oxo($C_4$-$C_6$)alken-2-yl, phenyl($C_1$-$C_6$) alkyl, phenyl($C_2$-$C_6$)alkenyl, gem-diphenyl($C_1$-$C_6$)alkyl, gem-diphenyl($C_2$-$C_6$)alkenyl, ($C_1$-$C_6$)alcanoyl, optionally N-substituted alanyl, optionally N,N'-disubstituted lysinoyl, phenyl($C_1$-$C_6$)alkylydene or gem-diphenyl($C_1$-$C_6$)alkylidene group, and of the pharmaceutically acceptable salts thereof, for preparation of medicaments intended for the treatment of CNS diseases due to reduced glycinergic transmission, particularly for the treatment of autism, schizophrenia and Alzheimer's disease, is described.

11 Claims, No Drawings

DERIVATIVES OF GLYCINERGIC R(+)-2-AMINO-3-HYDROXYPROPANOIC ACID

This application is a National Stage of International Application PCT/FR2003/002447, filed Aug. 1, 2003; which claims the priority of FR02/10306, filed Aug. 14, 2002.

OBJECT OF THE INVENTION

The present invention concerns the use of R(+)-2-amino-3-hydroxypropanoic acid derivatives for preparing medicaments for the treatment of Central Nervous System (CNS) diseases due to reduced glycinergic transmission, pharmaceutical compositions comprising new R(+)-2-amino-3-hydroxypropanoic acid derivatives as active principles, as well as new R(+)-2-amino-3-hydroxypropanoic acid derivative compounds.

BACKGROUND OF THE INVENTION

Following the discovery of the glycine binding site coupled to the NMDA receptor at the level of CNS, it has been suggested that a deficiency in glycinergic and/or glutaminergic transmission at the level of the NMDA receptor is one of the causes of diseases that involve cognitive and memory disorders such as autism, children learning disorders, schizophrenia and Alzheimer's disease.

Substances which are capable of enhancing glycinergic transmission are thus able of improving the cognitive disorders and mnestic disorders accompanying these diseases.

PRIOR ART

It is known that glycine is one of the most powerful agonists of the NMDA glycine site receptor and that other D-aminoacids, including D-serine, are very good agonists, but with a weaker affinity than that of glycine. An abstract journal on the subject was published in CNS Drug Reviews, 1995, 1(2), 227-260.

It is also known that the negative and cognitive symptoms of schizophrenia can be treated with glycine or with its precursors or even with glycine reuptake antagonists. In particular, documents U.S. Pat. Nos. 5,837,730 and 5,854,286 teach that very high oral doses (>30 g/day) of glycine or of compounds inducing elevations in CNS glycine level by serving as glycine precursors or which would substitute for glycine at the glycine site of the NMDA complex, lead to an improvement in the negative symptoms in schizophrenic patients. Among these compounds, the documents mention glycinamide, threonine and D-serine.

U.S. Pat. No. 6,228,875 shows that neuropsychiatric diseases characterized by a deficiency in neurotransmission by NMDA receptor can be alleviated by means of a composition acting as an agonist of the glycine site on NMDA receptor. Among these agonists, said document notably mentions D-serine, D-serine esters, alkylated D-serine or D-serine precursors. The same document describes a double-blind clinical trial in which D-serine, administrated at a dose of 2 g/day, is effective in the treatment of schizophrenia, even in patients having little response to conventional antipsychotic drug treatment. The results of the study described in this document lead to the conclusion that D-serine, which despite having a lower affinity than glycine is clinically active in a dose 15 times weaker than that expected for glycine, is undoubtedly not just a mere glycine substitute.

SUMMARY OF THE INVENTION

Now it has been discovered that D-serine derivatives, namely R(+)-2-amino-3-hydroxypropanoic acid derivatives, evaluated in predictive tests for an improvement in the activity of glycinergic transmission, have proven to be superior to D-serine.

More particularly, it has been found that R(+)-2-amino-3-hydroxypropanoic acid, substituted on nitrogen with a ($C_3$-$C_6$)alkenyl, 3-oxo($C_5$-$C_6$)alkyl, 3-oxo($C_4$-$C_6$)alken-2-yl, phenyl($C_1$-$C_6$)alkyl, phenyl($C_2$-$C_6$)alkenyl, gem-diphenyl($C_1$-$C_6$)alkyl, gem-diphenyl($C_2$-$C_6$)alkenyl, ($C_1$-$C_6$)alcanoyl, optionally N-substituted 2-aminopropionyl, optionally N,N'-disubstituted 2,6-diamino-n-hexanoyl, phenyl($C_1$-$C_6$) alkylidene or gem-diphenyl($C_1$-$C_6$)alkylidene group, notwithstanding its lower content in D-serine, is able to improve the glycinergic transmission in patients suffering from CNS diseases due to reduced glycinergic transmission, particularly patients suffering from autism, schizophrenia or Alzheimer's disease, in much weaker doses than those used for glycine and at the most as high as those used for D-serine.

It has also been found that, among said R(+)-2-amino-3-hydroxypropanoic acid derivatives, optionally esterified R(+)-2-amino-3-hydroxypropanoic acid, N-substituted by an alkyl group having at least one optionally substituted phenyl radical, has a higher in vivo activity than that of D-serine and of its alkylated derivatives.

DETAILED DESCRIPTION OF THE INVENTION

Thus, according to one of its aspects, the present invention concerns the use of a R(+)-2-amino-3-hydroxypropanoic acid derivative of formula I

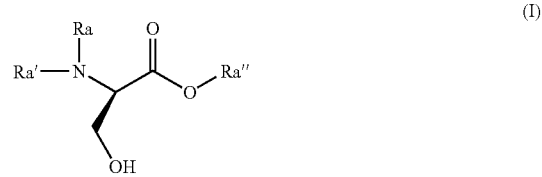

wherein Ra is a hydrogen, Ra' is a hydrogen, a straight or branched chain ($C_3$-$C_6$)alkenyl, 3-oxo($C_4$-$C_6$)alkyl or 3-oxo ($C_4$-$C_6$)alken-2-yl group, a phenyl($C_1$-$C_6$)alkyl, phenyl($C_2$-$C_6$)alkenyl, ($C_2$-$C_6$)alcanoyl, gem-diphenyl($C_1$-$C_6$)alkyl, gem-diphenyl($C_2$-$C_6$)alkenyl, ($C_3$-$C_6$)alkenoyl, R(+)-2-aminopropionyl, S(−)-2-aminopropionyl, N-($C_2$-$C_6$)alcanoyl-R(+)-2-aminopropionyl, N-($C_2$-$C_6$)alcanoyl-S(−)-2-aminopropionyl, N-benzyloxycarbonyl-R(+)-2-aminopropionyl, N-benzyloxycarbonyl-S(−)-2-aminopropionyl, R(+)-2,6-diamino-n-hexanoyl, S(−)-2,6-diamino-n-hexanoyl, N,N'-bis-($C_2$-$C_6$)alcanoyl-R(+)-2,6-diamino-n-hexanoyl, N,N'-($C_2$-$C_6$)alcanoyl-S(−)-2,6-diamino-n-hexanoyl, N,N'-bis-benzyloxycarbonyl-R(+)-2,6-diamino-n-hexanoyl, N,N'-bis-benzyloxycarbonyl-S(−)-2,6-diamino-n-hexanoyl group; or Ra and Ra' are together a phenyl($C_1$-$C_6$)alkylidene or gem-diphenyl($C_1$-$C_6$)alkylidene group; Ra'' is a hydrogen, a straight or branched chain ($C_1$-$C_6$)alkyl or a ($C_3$-$C_6$)cycloalkyl($C_1$-$C_6$)alkyl, phenyl($C_1$-$C_2$)alkyl, phenacetyl or phenyl group, the phenyl group or groups present in the Ra, Ra' and Ra'' substituents being non-substituted or substituted by a halogen atom or by an hydroxy, ($C_1$-$C_3$)alkoxy, cyano, nitro or acetyl group, with the proviso that, when Ra and Ra' are both H, then Ra'' is other than hydrogen, methyl or ethyl;

or of a pharmaceutically acceptable salt thereof, for the preparation of medicaments for the treatment of cognitive disorders or mnestic disorders which accompany CNS diseases due to a reduced glycinergic transmission, particularly for the treatment of autism, schizophrenia and Alzheimer's disease.

Among the compounds of formula I wherein Ra' is a gem-diphenyl($C_1$-$C_6$)alkyl group, those in which Ra' is a ω-diphenyl($C_2$-$C_6$)alkyl group are particularly advantageous.

The activity of these products has been evaluated in a predictive test for this kind of activity that consists of evaluating animal locomotor activity. It is carried out on groups of 10 mice having received the testing compounds per os (8 mg/kg) 15 minutes before the injection of phencyclidine (4 mg/kg). The animals are placed in an "open field" divided into 9 equal squares. A camera records their activity during 25 minutes, locomotor activity being expressed as the number of squares crossed per minute.

Among the above-mentioned derivatives, the following known compounds, with the Chemical Abstracts Service registry number (CAS No.) given in brackets,
- isopropyl R(+)-2-amino-3-hydroxypropanoate (CAS No. 117426-05-8) and the pharmaceutically acceptable salts thereof, particularly hydrochloride (CAS No. 104055-30-3),
- benzyl R(+)-2-amino-3-hydroxypropanoate (CAS No. 133099-79-3) and pharmaceutically acceptable salts thereof, particularly hydrochloride (CAS No. 151651-44-4),
- N-[R(+)-2-aminopropionyl]-R(+)-2-amino-3-hydroxypropanoic acid (CAS No. 61427-68-7), and pharmaceutically acceptable salts thereof,
- N-[S(−)-2-aminopropionyl]-R(+)-2-amino-3-hydroxypropanoic acid (CAS No. 1115-50-0), and pharmaceutically acceptable salts thereof,
- N-[2-[S(−)-benzyloxycarbonylamino]propionyl]-R(+)-2-amino-3-hydroxypropanoic acid (CAS No. 17460-58-1), and pharmaceutically acceptable salts thereof,
- N-acetyl-R(+)-2-amino-3-hydroxypropanoic acid (CAS No. 152612-69-6), and pharmaceutically acceptable salts thereof,
- N-benzyl-R(+)-2-amino-3-hydroxypropanoic acid (CAS No. 106910-77-4), and pharmaceutically acceptable salts thereof,
- ethyl R(+)-N-[(1-methyl-3-oxo)-1-buten-1-yl]-2-amino-3-hydroxypropanoate and pharmaceutically acceptable salts thereof,
- R(+)-N-(3-phenyl)propyl-2-amino-3-hydroxypropanoic acid and pharmaceutically acceptable salts thereof,
- ethyl R(+)-N-(3-phenyl)propyl-2-amino-3-hydroxypropanoate and pharmaceutically acceptable salts thereof, are particularly advantageous for the intended use.

Compounds of formula I, particularly the above-mentioned specific compounds, are administered to patients in need of an increase of glycinergic transmission at a daily dose which does not exceed 10 g per day and which is advantageously between 200 and 7500 mg and more advantageously between 250-5000 mg. The preferred doses, 500 to 3000 mg or 750 to 2000 mg, allow a good improvement of glycinergic transmission and also improve the negative symptoms of schizophrenia, the symptoms of Alzheimer's disease and behavior in cases of autism.

For administration to patients, compounds which are useful as active principles destined to improve glycinergic transmission are included in pharmaceutical compositions formulated in unit dosages containing 10 mg to 1200 mg, advantageously 50 to 1000 mg of active principle.

According to another of its aspects, the present invention provides a pharmaceutical composition comprising, as active principle, a pharmacologically effective dose of a R(+)-2-amino-3-hydroxypropanoic acid derivative of formula II

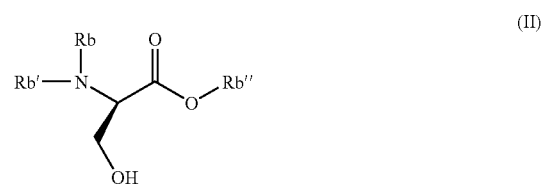

(II)

wherein Rb is a hydrogen, Rb' is a hydrogen, a straight or branched chain ($C_3$-$C_6$)alkenyl, 3-oxo($C_4$-$C_6$)alkyl or 3-oxo ($C_4$-$C_6$)alken-2-yl group, a phenyl($C_1$-$C_6$)alkyl, phenyl($C_2$-$C_6$)alkenyl, ($C_2$-$C_6$)alcanoyl, gem-diphenyl($C_1$-$C_6$)alkyl, gem-diphenyl($C_2$-$C_6$)alkenyl, ($C_3$-$C_6$)alkenoyl, N-($C_2$-$C_6$) alcanoyl-R(+)-2-aminopropionyl, N-($C_2$-$C_6$)alcanoyl-S(−)-2-aminopropionyl, N-benzyloxycarbonyl-R(+)-2-aminopropionyl, N-benzyloxycarbonyl-S(−)-2-aminopropionyl, R(+)-2,6-diamino-n-hexanoyl, S(−)-2,6-diamino-n-hexanoyl, N,N'-bis-($C_2$-$C_6$)alcanoyl-R(+)-2,6-diamino-n-hexanoyl, N,N'-($C_2$-$C_6$)alcanoyl-S(−)-2,6-diamino-n-hexanoyl, N,N'-bis-benzyloxycarbonyl-R(+)-2,6-diamino-n-hexanoyl, N,N'-bis-benzyloxycarbonyl-S(−)-2,6-diamino-n-hexanoyl group; or Rb and Rb' are together a phenyl($C_1$-$C_6$)alkylidene or gem-diphenyl($C_1$-$C_6$)alkylidene group; Rb" is hydrogen, a straight or branched chain ($C_1$-$C_6$)alkyl group or a ($C_3$-$C_6$) cycloalkyl($C_1$-$C_6$)alkyl, phenyl($C_1$-$C_2$)alkyl, phenacetyl or phenyl group, the phenyl group or groups present in the Rb, Rb' and Rb" substituents being non-substituted or substituted by a halogen atom or by a hydroxy, ($C_1$-$C_3$)alkoxy, cyano, nitro or acetyl group, with the proviso that, when Rb and Rb' are both H, then Rb" is other than hydrogen, methyl, ethyl or non-substituted benzyl and that, when Rb is hydrogen and Rb' is a non-substituted benzyl, N-benzyloxycarbonyl-S(−)-2-aminopropionyl, R(+)-2-aminopropionyl or S(−)-2-aminopropionyl, then Rb" is different to hydrogen; or of a pharmaceutically acceptable salt thereof, in admixture with a pharmaceutically acceptable carrier.

Among the compounds of formula II where Rb' is a gem-diphenyl($C_1$-$C_6$)alkyl group, those in which Rb' is a ω-diphenyl($C_2$-$C_6$)alkyl group, are particularly advantageous.

Among the above-mentioned active principles of formula II,
- 2-oxo-2-phenylethyl R(+)-2-amino-3-hydroxypropanoate and pharmaceutically acceptable salts thereof,
- cyclopropylmethyl R(+)-2-amino-3-hydroxypropanoate and pharmaceutically acceptable salts thereof,
- 4-acetylphenyl R(+)-2-amino-3-hydroxypropanoate and pharmaceutically acceptable salts thereof,
- N-[2-[R(+)-2,6-diaminohexanoyl]-R(+)-2-amino-3-hydroxypropanoic acid and pharmaceutically acceptable salts thereof,
- N-[2-[S(−)-2,6-diaminohexanoyl]-R(+)-2-amino-3-hydroxypropanoic acid, and pharmaceutically acceptable salts thereof,
- ethyl N-[S(−)-2-aminopropionyl]-R(+)-2-amino-3-hydroxypropanoate and pharmaceutically acceptable salts thereof,
- methyl N-[2-[S(−)-benzyloxycarbonylamino]propionyl]-R(+)-2-amino-3-hydroxypropanoate and pharmaceutically acceptable salts thereof, ethyl N-[2-[S(−)-benzyloxycarbonylamino]propionyl]-R(+)-2-amino-3-hydroxypropanoate and pharmaceutically acceptable salts thereof, N-[2-[R(+)-benzyloxycarbonylamino]propionyl]-R(+)-2-amino-3-hydroxypropanoic acid and pharmaceutically acceptable salts thereof, methyl N-[2-[R(+)-benzyloxycarbonylamino]propionyl]-R(+)-2-amino-3-hydroxypropanoate and pharmaceutically acceptable salts thereof, N-[2-[S(−)-N,N'-bis-benzyloxycarbonyl-2,6-diaminohexanoyl]-R(+)-2-amino-3-hydroxypropanoic acid and pharmaceutically acceptable salts thereof, methyl N-[2-[R(+)-N,N'-bis-benzyloxycarbonyl-2,6-diaminohexanoyl]-R(+)-2-amino-3-hydroxypropanoate and pharmaceutically acceptable salts thereof, methyl N-[2-[S(−)-N,N'-bis-benzyloxycarbonyl-2,6-diaminohexanoyl]-R(+)-2-amino-3-hydroxypropanoate and pharmaceutically acceptable salts thereof, ethyl N-[2-[R(+)-N,N'-bis-benzyloxycarbonyl-2,6-diaminohexanoyl]-R(+)-2-amino-3-hydroxypropanoate and pharmaceutically acceptable salts thereof, ethyl N-benzyl-R(+)-2-amino-3-hydroxypropanoate and pharmaceutically acceptable salts thereof, ethyl R(+)-N-[(1-methyl-3-oxo)-1-buten-1-yl]-2-amino-3-hydroxypropanoate and pharmaceutically acceptable salts thereof, R(+)-N-(3-phenyl)propyl-2-amino-3-hydroxypropanoic acid and pharmaceutically acceptable salts thereof, ethyl R(+)-N-(3-phenyl)propyl-2-amino-3-hydroxypropanoate and pharmaceutically acceptable salts thereof, are particularly interesting active principles.

In said pharmaceutical compositions for oral, sublingual, subcutaneous, intramuscular, transdermal or rectal administration, the active principle can be administrated in the most appropriate dosage unit in admixture with traditional pharmaceutical carriers in animals and humans. Suitable administration unit forms comprise oral forms such as tablets, capsules, powders, granulates and oral solutions or suspensions, sublingual and buccal administration forms or parenteral or rectal administration forms.

According to a further of its aspects, the present invention provides new R(+)-2-amino-3-hydroxypropanoic acid derivatives of formula III

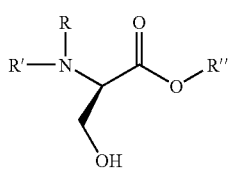

(III)

wherein R is a hydrogen; R' is a hydrogen, phenyl($C_2$-$C_6$)alkenyl, gem-diphenyl($C_1$-$C_6$)alkyl other than benzhydryl, gem-diphenyl($C_2$-$C_6$)alkenyl; or R and R' are together a phenyl($C_1$-$C_6$)alkylidene or gem-diphenyl($C_1$-$C_6$)alkylidene group; R'' is a hydrogen or a ($C_1$-$C_6$)alkyl, ($C_3$-$C_6$)cycloalkyl ($C_1$-$C_6$)alkyl, phenyl($C_1$-$C_2$)alkyl, phenacetyl or phenyl group; the phenyl group or groups being non-substituted or substituted by a halogen atom or by a hydroxy, ($C_1$-$C_3$) alkoxy, cyano, nitro or acetyl group, with the proviso that, when R and R' are both hydrogens, then R'' is other than hydrogen; and the pharmaceutically acceptable salts thereof.

Among the compounds of formula III in which R' is a gem-diphenyl($C_1$-$C_6$)alkyl group other than benzhydryl, those in which R' is a ω-diphenyl($C_2$-$C_6$)alkyl group are particularly advantageous.

Among the compounds of formula III,

R(+)-N-(4,4-diphenyl)butyl-2-amino-3-hydroxypropanoic acid and pharmaceutically acceptable salts thereof, R(+)-N-[(4,4-diphenyl)-3-butenyl]-2-amino-3-hydroxypropanoic acid and pharmaceutically acceptable salts thereof, and R(+)-N-[(α-phenyl-(2-hydroxy)benzylidene]-2-amino-3-hydroxypropanoic acid and pharmaceutically acceptable salts thereof are particularly advantageous.

The compounds of the invention, which are N-substitution derivatives of the R(+)-2-amino-3-hydroxypropanoic acid or of the esters thereof, and the pharmaceutically acceptable salts thereof, are synthesized according to the traditional preparation methods of amino acid esters or of N-substituted amino acid derivatives and of their esters.

R(+)-2-amino-3-hydroxypropanoic acid esters can be obtained by reacting a D-serine functional derivative with an esterifying alcohol or phenol or by saponification in position 4 of the methyl or ethyl (R)-3-tert-butoxycarbonyl-2,2-dimethyloxazolidine-4-carboxylate, esterification of the (R)-3-tert-butoxycarbonyl-2,2-dimethyloxazolidine-4-carboxylic acid by reaction of a functional derivative thereof with the esterifying alcohol or phenol in the presence of a proton acceptor, for example of a tertiary base such as 4-dimethylaminopyridine, methylmorpholine, ethylmorpholine or diisopropylamine, and saponification of tert-butyl ester with trifluoroacetic acid which concurrently affords the decomposition of the oxazolidine cycle and the formation of the desired R(+)-2-amino-3-hydroxypropanoic acid ester in form of its trifluoroacetic acid salt which, in its turn, can be neutralized or converted into another salt. The esters thus obtained can be transformed into N-substitution derivatives thereof and into pharmaceutically acceptable salts thereof.

N-monosubstitution can be carried out by reacting the R(+)-2-amino-3-hydroxypropanoic acid ester with an halide of formula:

Ra'-Hal (IVa), Rb'-Hal (IVb) or R'-Hal (IV)

wherein Ra', Rb' and R' have the above stated meanings, in the presence of an organic tertiary base such as 4-dimethylaminopyridine, 4-methyl- or 4-ethylmorpholine, or of an inorganic base such as an alkaline bicarbonate such as sodium hydrogen carbonate.

When Ra', Rb' and R' are optionally substituted alcanoyl groups, the corresponding acyl halide can be replaced by another functional derivative such as a mixed anhydride, an active ester or the free acid form, appropriately activated for example by dicyclohexylcarbodiimide. If the alcanoyl group is substituted on the alkyl with an amino group, the latter will be suitably protected by one of the conventional protecting groups of the peptide chemistry, for example by a benzyloxycarbonyl group.

In a similar way, the above halides, when Ra', Rb' or R' are other than an alcanoyl group, can be replaced by a compound of formula Ra'-X (IVa'), Rb'-X (IVb') or R'-X (IV')

wherein X represents a leaving group such as an alcanesulphonyloxy radical, such as a methanesulphonyloxy, or a benzenesulphonyloxy radical, the latter being non-substituted or substituted on the benzene cycle preferably with a methyl group, such as p-toluenesulphonyloxy.

Compounds of formula I, II or II, wherein Ra or Rb or R is hydrogen and Ra' or Rb' or R' is other than an alcanoyl group, can also be prepared by reductive amination by reacting the aldehyde or ketone corresponding to the compound Ra'-H or Rb'-H or R'-H with D-serine, preferably in the form of one of its esters, in the presence of a reducing agent such as sodium cyanoborohydride. If the ester has a group that is sensitive to reducing agents, for example a ketone, this group is suitably protected as a ketal or enol ether thereof.

The preparation of the compounds of formula I, II or III, wherein Ra and Ra', or Rb and Rb', or, respectively, R and R', together, form a phenyl($C_1$-$C_6$)alkylidene group, is carried out by reacting D-serine or an ester thereof with a phenyl($C_1$-$C_6$)carboxaldehyde under the preparation conditions of Schiff bases. In a similar way, the compounds of formula I, II or III, where Ra and Ra', or Rb and Rb', or R and R', together form a gem-diphenyl($C_1$-$C_6$)alkylidene group, are prepared by reacting D-serine or one of the esters thereof with a benzophenone, if the desired product has the formula I, II or III where Ra and Ra', or Rb and Rb', or R and R' together form a gem-diphenyl($C_1$)alkyl (diphenylmethyl) group; or with a gem-diphenyl($C_2$-$C_6$)carboxaldehyde, if the desired product has the formula I, II or III where Ra and Ra', or Rb and Rb', or R and R' together form a gem-diphenyl($C_2$-$C_6$)alkyl group, according to Schiff base preparation conditions.

The word "phenyl" used in the general description above, comprises any phenyl group that can be non-substituted or substituted by a halogen atom or by a hydroxy, ($C_1$-$C_3$) alkoxy, cyano, nitro or acetyl group.

When D-serine methyl or ethyl ester is used as starting compound, the N-substituted derivative thus obtained is an intermediate which is saponified in order to prepare a compound of formula I, II or III wherein Ra", Rb" or R" is hydrogen, whereas the N-substituted derivative thus obtained is the final product when an ester other than the methyl or ethyl ester is used as starting compound.

The R(+)-2-amino-3-hydroxypropanoic acid derivatives can be isolated in the free form or as chemically or pharmaceutically acceptable salts thereof. Considering the amphoteric character of the compounds of the present invention, the salts can be those with mineral or organic bases, for example with sodium hydroxide or trometamol, or with mineral or organic acids such as the hydrochloride or the trifluoroacetate. In the case of the compounds of formula I, chemically or pharmaceutically acceptable salts are included in the invention. The expression "chemically acceptable" refers to salts of formula I compounds that are useful for the isolation or purification of the new products.

The following non-limitative examples illustrate the invention.

EXAMPLE 1

Cyclopropylmethyl 2-(R)-amino-3-hydroxypropanoate hydrochloride

Cyclopropylcarbinol (15 ml) is cooled to 0° C. and acetyl chloride (1.37 ml) is added. After being subjected to agitation for 10 minutes at 0° C., D-serine (750 mg) is added and the solution is brought to reflux for 2 hours. The reaction mixture is concentrated, recovered with a potassium carbonate saturated solution and extracted with ethyl acetate. The organic phase is dried on $MgSO_4$, filtered and concentrated. The product is recovered in a minimum of methanol and a hydrochloric acid solution 1N is added in ether. The solvent is vacuum evaporated to obtain the desired product as a brown solid (250 mg). Melting point: 112-118° C.

RMN $^1$H ($CD_3OD$) d 4.07 (m, 5H); 1.18 (m, 1H); 0.64 (m, 2H); 0.37 (m, 2H).

EXAMPLE 2

4-acetylphenyl 2-(R)-amino-3-hydroxypropanoate trifluoroacetate (a) methyl 3-tert-butoxycarbonyl-2,2-dimethyloxazolidine-4-(R)-carboxylate The product is prepared according to the method described in the article of P. Garner, J. M. Park, J. Org. Chem. 1987, 52, 2361-2364.

(b) 3-tert-butoxycarbonyl-2,2-dimethyloxazolidine-4-(R)-carboxylic acid

Methyl 3-tert-butoxycarbonyl-2,2-dimethyloxazolidine-4-(R)-carboxylate (3.0 g) is dissolved in a mixture of tetrahydrofurane (THF)/$H_2O$ (3/1; 30 ml), and LiOH.$H_2O$ (684 mg) is added. After being subjected to agitation for 3 hours at room temperature, the reaction mixture is acidified with citric acid 1N (11 ml). THF is concentrated and the aqueous phase is extracted with ethyl acetate. The organic phase is dried on $MgSO_4$, filtered and concentrated to obtain the expected product as a viscous orange oil (1.36 g).

(c) 4-acetylphenyl 3-tert-butoxycarbonyl-2,2-dimethyloxazolidine-4-(R)-carboxylate At 0° C., 3-tert-butoxycarbonyl-2,2-dimethyloxazolidine-4-(R)-carboxylic acid (1.0 g) is dissolved in ethyl acetate (25 ml), dicyclohexylcarbodiimide (DCC; 1.26 g) is then added and the reaction mixture is subjected to agitation for 45 minutes at 0° C. Dimethylaminopyridine (DMAP; 100 mg) and 4'-hydroxyacetophenone (565 mg) are successively added, the reaction mixture is then left to return to room temperature. After 5 hours of agitation, the mixture is filtered and the filtrate is washed with a sodium hydrogen carbonate saturated solution, then with a sodium chloride saturated solution. The organic phase is dried on $MgSO_4$, filtered and concentrated. The obtained orange oil is purified by chromatography on silica to obtain the desired product as a transparent oil (940 mg).

(d) 4-acetylphenyl 2-(R)-amino-3-hydroxypropanoate trifluoroacetate

Under nitrogen, 4-acetylphenyl 3-tert-butoxycarbonyl-2,2-dimethyloxazolidine-4-(R)-carboxylate (440 mg) is dissolved in dichloromethane (15 ml), and trifluoroacetic acid (TFA; 8 ml) is added. After being subjected to agitation for 1 hour, the reaction mixture is concentrated and ether is added. The formed precipitate is filtered, then vacuum dried to obtain the desired product as a white powder (280 mg). Melting point: 115-118° C.

RMN $^1$H ($CD_3OD$) d 8.12 (d, 2H); 7.39 (d, 2H); 4.49 (m, 1H); 4.25 (dd, 1H); 4.08 (dd, 1H); 2.56 (s, 3H).

EXAMPLE 3

Ethyl N-[2-[S(−)-benzyloxycarbonylamino]propionyl]-R(+)-2-amino-3-hydroxypropanoate At 0° C., N-benzyloxycarbonyl-S(−)-alanine (3.0 g), R(+)-serine ethyl ester hydrochloride (2.28 g), 1-hydroxybenzotriazole hydrate (HOBt.$H_2O$; 1.82 g) and N-ethylmorpholine (1.69 ml) are dissolved in tetrahydrofurane (THF; 30 ml).

Then dicyclohexylcarbodiimide (DCC) (2.91 g) is added and the mixture is left to return to room temperature. After being subjected to agitation for 5 hours, the solution is filtered, rinsed with THF and the filtrate is concentrated. The residue is recovered in dichloromethane and the organic phase is successively washed with a sodium carbonate saturated solution, water and a sodium chloride saturated solution. The organic phase is dried on $MgSO_4$, filtered and concentrated. The obtained solid is purified by chromatography on silica to obtain the desired product as a white powder (2.5 g).

EXAMPLE 4

Ethyl N-[S(−)-2-aminopropionyl]-R(+)-2-amino-3-hydroxypropanoate hydrochloride

The ethyl N-[2-[S(−)-benzyloxycarbonylamino]propionyl]-R(+)-2-amino-3-hydroxypropanoate (1.0 g) obtained as described in example 3, is dissolved in ethanol (25 ml), and a concentrated hydrochloric acid solution (0.25 ml) and palladium on carbon (150 mg) are added. The reaction mixture is placed under hydrogen atmosphere (P=1.3 bar) for 30 minutes, then filtered on kelite. The filtrate is dry evaporated to obtain the desired product as a beige powder (635 mg). Melting point: 163-168° C.

RMN $^1$H ($CD_3OD$) d 4.55 (m, 1H); 4.21 (q, 2H); 4.05 (m, 1H); 3.9 (m, 2H); 1.54 (d, 3H); 1.28 (t, 3H).

EXAMPLE 5

Ethyl N-[2-[R(+)-N,N'-bis-benzyloxycarbonyl-2,6-diaminohexanoyl]-R(+)-2-amino-3-hydroxypropanoate At 0° C., N,N'-bis-benzyloxycarbonyl-R(+)-lysine (2.51 g), R(+)-serine ethyl ester hydrochloride (1.03 g), $HOBt.H_2O$ (0.82 g) and N-ethylmorpholine (0.76 ml) are dissolved in THF (30 ml). Then DCC (1.31 g) is added and the medium is left to return to room temperature for 4 hours. The reaction mixture is filtered on sintered material, washed with THF then the filtrate is dry concentrated. The residue is recovered in ethyl acetate and the organic phase is washed with a sodium carbonate saturated solution, then with a sodium chloride saturated solution. The organic phase is dried on $MgSO_4$, filtrated and concentrated. The obtained solid is purified by chromatography on silica to obtain the desired product as a white solid (1.14 g). Melting point: 133-136° C.

RMN $^1$H ($CDCl_3$) d 7.28 (brs, 10H); 6.94 (brs, NH); 5.55 (brs, NH); 5.11 (s, 2H); 5.08 (s, 2H); 4.99 (brs, NH); 4.62 (m, 1H); 4.22 (q, 3H); 3.96 (brs, 2H); 3.21 (m, 2H); 1.72 (m, 6H); 1.27 (t, 3H).

EXAMPLE 6

Methyl R(+)-N-(4,4-diphenyl)butyl-2-amino-3-hydroxypropanoate (a) 1,1-Diphenyl-4-bromobutene At 0° C., cyclopropyl-diphenyl-carbinol (10.0 g) is dissolved in a hydrogen bromide solution 48% (40 ml). After being subjected to agitation for 5 hours at 0° C., the medium is diluted with water and dichloromethane, then the organic phase is washed three times with water. The organic phase is dried on $MgSO_4$, filtered and concentrated to obtain the expected product as an orange oil (11.89 g).

(b) 1,1-Diphenyl-4-bromobutane 1,1-diphenyl-4-bromobutene (10.0 g) is dissolved in absolute ethanol (100 ml) and palladium on carbon (400 mg) is added. The reaction mixture is placed under hydrogen atmosphere (P=3.3 bar) for 6 hours. The mixture is filtered on kelite, the filtrate is concentrated to obtain the desired product as an orange oil (9.24 g).

(c) methyl R(+)-N-(4,4-diphenyl)butyl-2-amino-3-hydroxypropanoate

D-serine ethyl ester hydrochloride (1.5 g) is dissolved in dimethylformamide (DMF; 20 ml), sodium hydrogen carbonate (1.78 g) is added and 1,1-diphenyl-4-bromobutane (3.35 g) is dissolved in DMF (5 ml). The reaction mixture is raised to 85° C. for 1 hour, then vacuum concentrated. The residue is recovered with ethyl acetate and water, then the organic phase is washed three times with a sodium chloride saturated solution. The organic phase is dried on $MgSO_4$, filtered and vacuum concentrated. Purification by chromatography on silica to obtain the desired product as a loose yellow oil (1.38 g).

EXAMPLE 7

R(+)-N-(4,4-diphenyl)butyl-2-amino-3-hydroxypropanoic acid hydrochloride

At 0° C., methyl R(+)-N-(4,4-diphenyl)butyl-2-amino-3-hydroxypropanoate (600 mg) is dissolved in a $THF/H_2O$ mixture (3/1; 20 ml) and a sodium hydroxide solution 5N (0.7 ml) is added. After 15 minutes at 0° C., the reaction mixture is left to return to room temperature. After 45 minutes, the mixture is cooled again to 0° C., a hydrochloric acid solution 1N (4 ml) is added, the mixture is then vacuum concentrated. The solid obtained is triturated in boiling isopropanol and the mixture is hot filtered. After evaporation of the filtrate, the desired product is obtained as a clear yellow powder (303 mg). Melting point: 70-75° C.

RMN $^1$H ($CD_3OD$) d 7.18 (brs, 7H); 7.05 (m, 3H); 3.88 (m, 2H); 3.83 (m, 2H); 3.00 (m, 1H); 2.08 (m, 2H); 1.61 (m, 2H); 1.24 (m, 2H).

EXAMPLE 8

Methyl R(+)-N-[(4,4-diphenyl)-3-butenyl]-2-amino-3-hydroxypropanoate

R(+)-serine methyl ester hydrochloride (1.0 g) is dissolved in dimethylformamide (DMF), sodium hydrogen carbonate (1.08 g) and 1-(4-bromo-1-phenylbut-1-enyl) benzene (2.03 g) are added. After being subjected to agitation overnight at room temperature the medium is vacuum concentrated. The residue is recovered in ethyl acetate then the organic phase is washed three times with water. The organic phase is dried on $MgSO_4$, filtered and concentrated. The desired product is obtained as a white powder (600 mg).

EXAMPLE 9

R(+)-N-[(4,4-diphenyl)-3-butenyl]-2-amino-3-hydroxypropanoic acid hydrochloride

At 0° C., methyl R(+)-N-[(4,4-diphenyl)-3-butenyl]-2-amino-3-hydroxypropanoate (600 mg) is dissolved in a mixture of $THF/H_2O$ (3/1; 20 ml), then a sodium hydroxide solution 5N (700 µL) is added. After being subjected to agitation for 15 minutes at 0° C., the reaction mixture is left to return to room temperature for 45 minutes and then the solution is cooled again to 0° C. A hydrochloric acid solution 1N (4 ml) is added and the medium is vacuum concentrated. The white solid obtained is triturated in boiling isopropanol, then filtered. After evaporation of the filtrate, the desired product is obtained as a clear yellow foam (303 mg). Melting point: 130-135° C.

RMN $^1$H (CD$_3$OD) d 7.31 (m, 3H); 7.15 (m, 6H); 6.00 (t, 1H); 3.79 (m, 3H); 3.08 (m, 2H); 2.44 (m, 2H).

EXAMPLE 10

Ethyl R(+)-N-(3-phenyl)propyl-2-amino-3-hydroxypropanoate

R(+)-serine ethyl ester hydrochloride (1.0 g) is left in suspension in anhydrous methanol, the molecular sieve 4 Å and sodium cyanoborohydride (NaBH$_3$CN, 267 mg) are added. After being subjected to agitation for 15 minutes, 3-phenyl-propionaldehyde (705 µL) is added in one portion. After being subjected to agitation for 3 h30 at room temperature, the reaction mixture is filtered on sintered material and the filtrate is concentrated. The recovered viscous transparent oil (1.95 g) is purified by chromatography on silica to obtain a loose clear yellow oil (900 mg). The residue is recovered with a minimum of ether and a hydrochloric acid solution 1N is added in ether (6 ml). The precipitate formed is filtered, then dried to obtain the desired product as a white solid (990 mg). Melting point: 102-107° C.

RMN $^1$H (CD$_3$OD) d 7.25 (m, 5H); 4.30 (q, 2H); 4.11 (m, 1H); 3.9 (m, 2H); 3.29 (m, 1H); 3.08 (m, 2H); 2.71 (t, 2H); 2.05 (m, 2H); 1.38 (t, 3H).

EXAMPLE 11

R(+)-N-(3-phenyl)propyl-2-amino-3-hydroxypropanoic acid hydrochloride

The ethyl R(+)-N-(3-phenyl)propyl-2-amino-3-hydroxypropanoate of example 10 (600 mg) is dissolved in a mixture of THF/H$_2$O (3/1; 20 ml) and LiOH.H$_2$O (175 mg) is added. After being subjected to agitation overnight at room temperature, the THF is concentrated and a hydrochloric acid solution 1N (2 ml) is added. The precipitate formed is filtered, washed in water, then dried in a vacuum oven overnight to obtain the desired product as a white solid (290 mg). Melting point: 190-196° C.

RMN $^1$H (DMSO) d 7.25 (m, 5H); 3.73 (m, 1H); 3.62 (m, 1H); 3.20 (m, 1H); 2.85 (m, 2H); 2.58 (t, 2H); 1.90 (t, 2H).

EXAMPLE 12

Ethyl R(+)-N-[(1-methyl-3-oxo)-1-buten-1-yl]-2-amino-3-hydroxypropanoate

R(+)-serine ethyl ester hydrochloride (3.0 g) is dissolved in methanol (150 ml), 5 spatulas of molecular sieve 4 Å and then acetylacetone (2.55 ml) are added and the mixture is brought to reflux overnight. The solution is filtered on Kelite, rinsed with methanol and the filtrate is dry evaporated. The residue is recovered with ethyl acetate, ether is added, the filtrate is triturated, filtered and concentrated. Purification by chromatography on silica to obtain the desired product as a white solid (1.21 g). Melting point: 78° C.

RMN $^1$H (CDCl$_3$) d 11.00 (d, 1H); 5.00 (s, 1H); 4.23 (m, 4H); 3.94 (m, 2H); 1.95 (m, 6H); 1.27 (t, 3H).

EXAMPLE 13

R(+)-N-[α-phenyl-(2-hydroxy)benzylidene]-2-amino-3-hydroxypropanoic acid

Under nitrogen, R(+)-serine (1.0 g), o-hydroxybenzophenone (940 mg), sodium methanolate (512 mg) are dissolved in ethanol (50 ml) and the reaction mixture is brought to reflux for 3 hours. The medium is vacuum concentrated and recovered in ether. A concentrated citric acid solution is added and the aqueous phase is extracted with ether. The organic phase is dried on MgSO$_4$, filtered and concentrated. The residue is recovered in a minimum of ether, triturated and filtered to obtain the desired product as a yellow powder (610 mg). Melting point: 170° C.

RMN $^1$H (CD$_3$OD) d 7.58 (m, 3H); 7.34 (m, 3H); 6.95 (m, 1H); 6.82 (m, 1H); 6.67 (m, 1H); 4.17 (m, 1H); 3.95 (m, 2H).

The invention claimed is:

1. A R(+)-2-amino-3-hydroxypropanoic acid derivative of formula III, or one of its pharmaceutically acceptable salts;

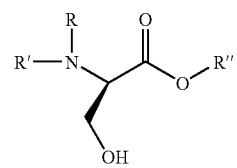

(III)

wherein R is hydrogen;
R' is hydrogen, or a phenyl(C$_2$-C$_6$)alkenyl group, or a gem-diphenyl(C$_1$-C$_6$)alkyl group other than benzhydryl, or a gem-diphenyl(C$_2$-C$_6$)alkenyl group; or
R and R', together, form a phenyl(C$_1$-C$_6$)alkylidene or gem-diphenyl(C$_1$-C$_6$)alkylidene group;
R" is hydrogen or a (C$_1$-C$_6$)alkyl, (C$_3$-C$_6$)cycloalkyl(C$_1$-C$_6$)alkyl, phenyl(C$_1$-C$_2$)alkyl or phenacetyl group;
the phenyl group or groups being non-substituted or substituted by a halogen atom or by a hydroxy, (C$_1$-C$_3$) alkoxy, cyano, nitro or acetyl group;
with the proviso that, when R and R' are both hydrogen, then R" is other than hydrogen, (C$_1$-C$_6$)alkyl or non-substituted benzyl.

2. The R(+)-2-amino-3-hydroxypropanoic acid derivative according to claim 1, where R' is a ω-diphenyl(C$_2$-C$_6$)alkyl group.

3. R(+)-N-(4,4-diphenyl)butyl-2-amino-3-hydroxypropanoic acid or a pharmaceutically acceptable salt thereof.

4. R(+)-N-[(4,4-diphenyl)-3-butenyl]-2-amino-3-hydroxypropanoic acid or a pharmaceutically acceptable salt thereof.

5. R(+)-N-[α-phenyl-(2-hydroxy)benzylidene]-2-amino-3-hydroxypropanoic acid or a pharmaceutically acceptable salt thereof.

6. A method for treating schizophrenia, comprising administering to a patient the R(+)-2-amino-3-hydroxypropanoic acid derivative according to claim 1.

7. The method according to claim 6, wherein said treatment increases glycinergic transmission in said patient.

8. The R(+)-2-amino-3-hydroxypropanoic acid derivative according to claim 1, wherein R' is a phenyl(C$_2$-C$_6$)alkenyl.

9. The R(+)-2-amino-3-hydroxypropanoic acid derivative according to claim 1, which is R(+)-N-(4,4-diphenyl)butyl-2-amino-3-hydroxypropanoic acid hydrochloride.

10. The R(+)-2-amino-3-hydroxypropanoic acid derivative according to claim 1, which is methyl R(+)-N-[(4,4-diphenyl)-3-butenyl]-2-amino-3-hydroxypropanoate.

11. A pharmaceutical composition comprising a pharmaceutically effective dose of the R(+)-2-amino-3-hydroxypropanoic acid derivative according to claim 1, or one of its pharmaceutically acceptable salts, in admixture with a pharmaceutically acceptable carrier.

* * * * *